United States Patent [19]

Anderson et al.

[11] Patent Number: 4,947,682
[45] Date of Patent: Aug. 14, 1990

[54] METHOD OF LOCATING OIL AND GAS HORIZONS USING A WELLBORE HEAT FLOW LOG

[75] Inventors: Roger N. Anderson, New York, N.Y.; Colin F. Williams, Menlo Park, Calif.

[73] Assignee: The Trustees of Columbia University in the City of New York, New York, N.Y.

[21] Appl. No.: 322,790

[22] Filed: Mar. 13, 1989

[51] Int. Cl.⁵ .............................................. E21B 47/06
[52] U.S. Cl. ....................................... 73/154; 374/136; 436/29
[58] Field of Search .................. 73/152, 154; 374/136; 166/60, 250; 175/50; 436/25, 28, 29

[56] References Cited

U.S. PATENT DOCUMENTS

| | | | |
|---|---|---|---|
| 3,217,550 | 11/1965 | Birman | 73/154 |
| 3,864,969 | 2/1975 | Smith, Jr. | 73/154 |
| 3,892,128 | 7/1975 | Smith, Jr. | 73/154 |
| 4,120,199 | 10/1978 | Mufti | 73/154 |
| 4,575,260 | 3/1986 | Young | 73/154 |
| 4,676,664 | 6/1987 | Anderson et al. | 73/154 |

OTHER PUBLICATIONS

Drury, M. J. and Jessop, A. M., "The Estimation of Rock Thermal Conductivity from Mineral Content—An Assessment of Techniques," Zbl. Geol. Paleont, Teil I, 1983; pp. 35–48.
Herzog, R., L. Colson, B. Seeman, M. O'Brien, H. Scott, D. McKeon, P. Wraight, J. Grau, J. Schweitzer, and M. Herron, "Geochemical Logging with Spectrometry Tools," Society of Petroleum Engineers, Paper 16792, 1987.
Meyer, H. J. and McGee, H. W., "Oil and Gas Fields Accompanied by Geothermal Anomalies in Rocky Mountain Region," Am. Assoc. Petr. Geol. Bull. 69, No. 6, 1986, pp. 933–945.
Roberts, W. H. III, "Some Uses of Temperature Data in Petroleum Exploration in Unconventional Methods in Exploration for Petroleum and Natural Gas," II, ed. B. M. Gottlieb, Inst. Study of Earth and Man, SMU Press, Dallas, 1981, pp. 8–49.
Williams, C. F., Anderson, R. N., and Broglia, C., "In Situ Investigations of Thermal Conductivity, Heat Production, and Past Hydrothermal Circulation in the Cajon Pass Scientific Drill Hole," Geophys. Res. Lett., 15, 9, 1988, pp. 985–988.

*Primary Examiner*—Hezron E. Williams
*Assistant Examiner*—Kevin D. O'Shea
*Attorney, Agent, or Firm*—Brumbaugh, Graves, Donohue & Raymond

[57] ABSTRACT

Oil and gas horizons in a wellbore are located by establishing from thermal logs thermal gradients for successive intervals free of drilling-induced thermal disturbances, identifying the mineral abundances surrounding the wellbore at each of said intervals, establishing ideal thermal conductivities for said mineral abundances based on assumptions that sand-rich formations have high thermal conductivities and are water-bearing and that shale-rich formations have low conductivities, determining an ideal heat flow at each interval by multiplying the thermal gradient at such interval by the ideal thermal conductivity of the mineral abundances at the interval, determining the average ideal heat flow for all of the intervals, and identifying the zones of the wellbore exhibiting anomalous ideal heat flows that are higher than the average heat flow.

6 Claims, 4 Drawing Sheets

THERMAL CONDUCTIVITY DETERMINED FROM MINERALOGY LOG

METHOD OF LOCATING OIL AND GAS HORIZONS USING A WELLBORE HEAT FLOW LOG

BACKGROUND OF THE INVENTION

Thermal gradients are commonly used in the oil industry to determine the thermal state of the subsurface. Examples of correlations between variations in thermal gradients and oil and gas horizons in fields within the United States can be found in the literature as far back as the 1920's. More recent examples of such correlations are presented in Meyer, H. J. and McGee, H. W., "Oil and Gas Fields Accompanied by Geothermal Anomolies in Rocky Mountain Region," Am. Assoc. Petr. Geol. Bull. 69, No. 6, 1986, pp. 933–45. An excellent review of this methodology can be found in Roberts, W. H. III, "Some Uses of Temperature Data in Petroleum Exploration in Unconventional Methods in Exploration for Petroleum and Natural Gas," II, ed. B. M. Gottlieb, Inst. Study of Earth and Man, SMU Press, Dallas 1981.

Though the occurrences of oil and gas production zones are sometimes found associated with thermal gradient changes, the correlation has not proved to be consistent. The drilling history of the well severely disturbs the ambient thermal gradients surrounding the well, and equilibrium corrections that must be made to raw temperature measurements are very complicated. Multiple temperature logs, run at several different times in a well, greatly improve the data quality, but such multiple logs are rarely available.

Several techniques have been proposed to measure the thermal conductivity variations, instead of thermal gradients, of the earth formations and fluids in and around a wellbore. In Smith U.S. Pat. No. 3,864,969 for "Station Measurements of Earth Formation Thermal Conductivity" (1975), it is shown that oil and gas bearing horizons have 50–100% lower thermal conductivities than similar lithogies that are water-bearing (FIG. 1). In Smith U.S. Pat. No. 3,892,128 for "Methods of Thermal Well Logging" (1975), there is described a technique for directly logging thermal conductivity in a well in order to determine the locations of oil and gas bearing formations. A special logging tool with a heat source is dragged up the borehole, and the rate of diffusion of heat from the tool into the rock is measured. Similarly, Young U.S. Pat. No. 4,575,260 for "Thermal Conductivity Probe for Fluid Identification" (1986) describes a heater-probe for a logging tool that measures the thermal conductivity of the wellbore fluid, rather than that of the rock. If hydrocarbons are present in the well, the thermal conductivity probe will detect unusually low thermal conductivities.

Neither the measurement of thermal gradient nor thermal conductivity in wells has proved to be a consistent locator of hydrocarbons. The measurement of thermal gradients and thermal conductivities separately in a well gives inconsistent results for the detection of thermal anomalies associated with oil and gas-bearing horizons for a fundamental scientific reason: each alone does not measure the proper physical parameter. The flow of heat from the earth is not measured by either the thermal conductivity or the thermal gradient, but by the product of these two physical properties. Heat flow equals thermal gradient times thermal conductivity at any given depth in a wellbore. If both accurate thermal gradients and thermal conductivities can be ascertained throughout a wellbore, the heat flow at every depth in a well can be calculated.

Determination of heat flow allows the application of fundamental physical laws to the interpretation of hydrocarbon migration and fluid flow in the subsurface. For example, heat flow must be constant with depth if a wellbore is in thermal equilibrium. Fluid convection, geopressuring, and oil and gas migration can all produce heat flow that is not constant with depth in a wellbore. Thus, the thermal gradient at any point in a well may be found to be high because of either low thermal conductivity (e.g., due solely to a lithology change), or because hot, low thermal conductivity fluids have recently migrated into traps penetrated by the wellbore. From the wellbore heat flow, however, it is possible to determine not only the likely locations and possible compositions of hydrocarbons in the vicinity of the well, but also whether fluid flow is active in the region surrounding the wellbore.

SUMMARY OF THE INVENTION

There is provided, according to the present invention, a method of locating oil and gas horizons in a wellbore based on determinations of the heat flows at successive intervals in the wellbore. The method comprises the steps of: obtaining by thermal logging temperatures at successive equal intervals in the wellbore and establishing from said temperatures thermal gradients for said intervals free of drilling-induced thermal disturbances; identifying the mineral abundances surrounding the wellbore at each of said intervals; establishing ideal thermal conductivities for said mineral abundances based on assumptions that sand-rich formations have high thermal conductivities and are water-bearing and that shale-rich formations have low conductivities; determining an ideal heat flow at each interval by multiplying the thermal gradient at such interval by the ideal thermal conductivity of the mineral abundances at the interval; determining the average ideal heat flow for all of the intervals, and identifying the zones of the wellbore exhibiting anomalous ideal heat flows that are higher than the average heat flow.

The critical beginning of an accurate determination of wellbore heat flow is to log the change in temperature with depth, the thermal gradient, accurately in a well. The thermal gradient must be either recorded at two or more different times during a logging operation or at a sufficiently long time after drilling has ceased for the disturbances caused by the drilling procedure to have dissipated. Thermal disturbances, such as from increased or lost circulation, can be recognized and corrected for if multiple temperature logs exist in a well. Drilling-induced thermal disturbances will be present on both logs, but the differences between the temperatures measured at different times allows for the identification of, and correction for, these effects.

Although many methods have been investigated for the determination of thermal conductivities from geophysical logs (e.g., Williams, C. F., Anderson, R. N., and Broglia, C., "In Situ Investigations of Thermal Conductivity, Heat Production, and Past Hydrothermal Circulation in the Cajon Pass Scientific Drill Hole," Geophys. Res. Lett., 15, 9, 985–988, 1988), the most reliable measurement techniques known currently appear to be those derived from mineral abundances determined by geochemical logging using, for example, the Schlumberger Geochemical Logging Tool (GLT TM), or when not available, by Phonon Conduction from Photoelectric-Density logs. In Drury, M. J. and Jessop, A. M., "The Estimation of Rock Thermal Conductivity from Mineral Content—An Assessment of Techniques," Zbl. Geol. Paleont, Teil I, 1983, it is shown that thermal conductivities accurate to 15% can be calculated from mineral abundances measured on core or cutting samples. This technique has long been used to place constraints on the thermal conductivity of the mantle, which is critical to models of the thermal history of the earth. In Williams, C. F. and Anderson, R. N., "Geophysical Properties of the Earth's Crust: In situ Measurements from Continental and Ocean Drilling," J. Geophys. Res. Submitted for publication, 1989, it is shown that the determination from mineral abundances from the GLT ™ tool produces log-derived thermal conductivities from mineral inversions that are also accurate to approximately 15%. Phonon conduction is somewhat less accurate, producing values good to perhaps 20%. In the present invention, identification of the mineral abundances can, therefore, be based on geochemical logs, photoelectric and density logs or core or cutting samples. Ideal thermal conductivities are established based on the identification of mineral abundances surrounding the wellbore and on the assumptions that sand-rich intervals have high thermal conductivities and have water as the pore fluid, and shale-rich intervals have low thermal conductivities.

An example of the method of the present invention, as applied in a Gulf Coast well, is described below in conjunction with the accompanying drawings.

DESCRIPTION OF THE EXAMPLE

Figure 2:
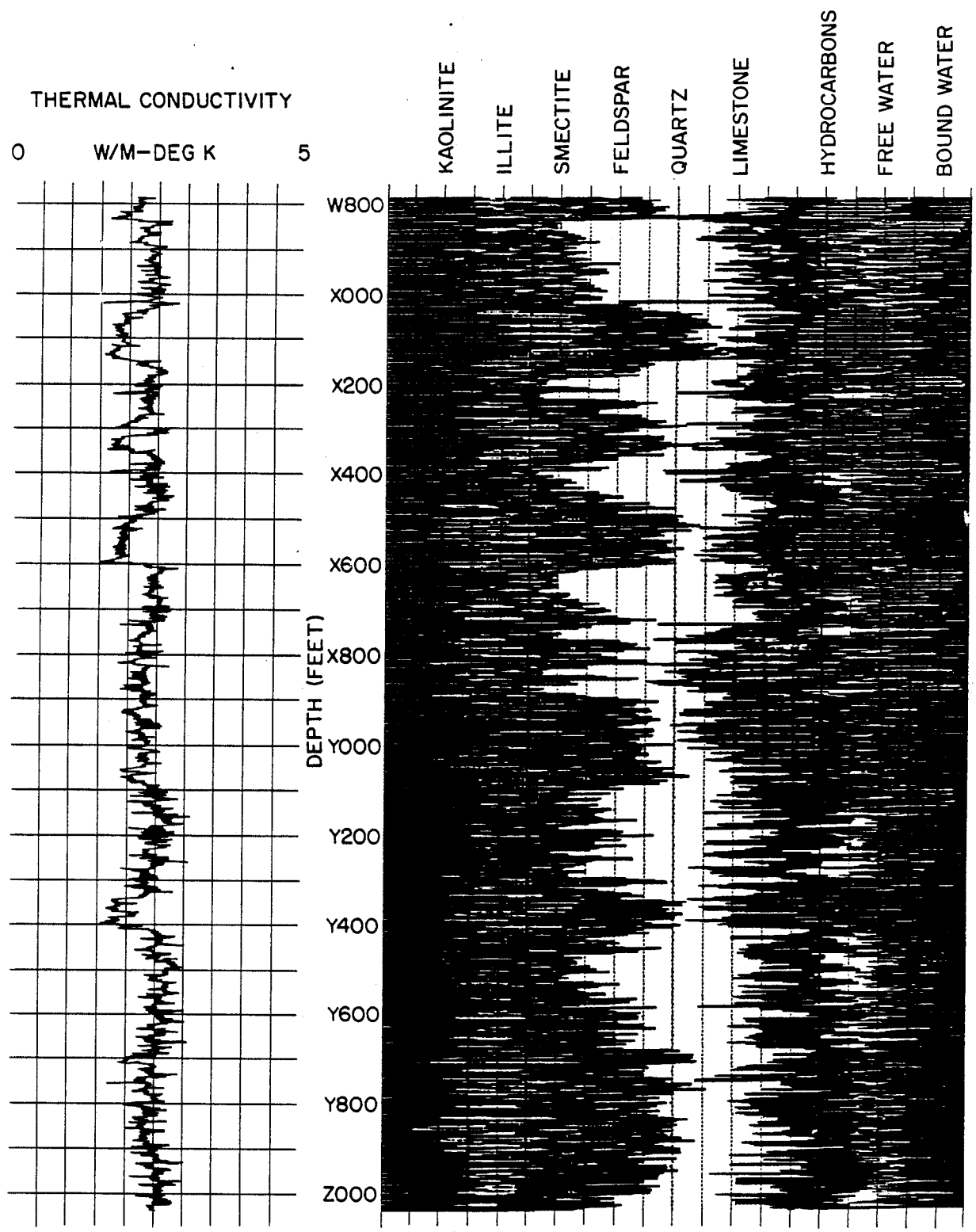
FIG. 2 shows at the right a mineralogy model of the well and at the left the thermal conductivity determined from the model.
Figure 3:
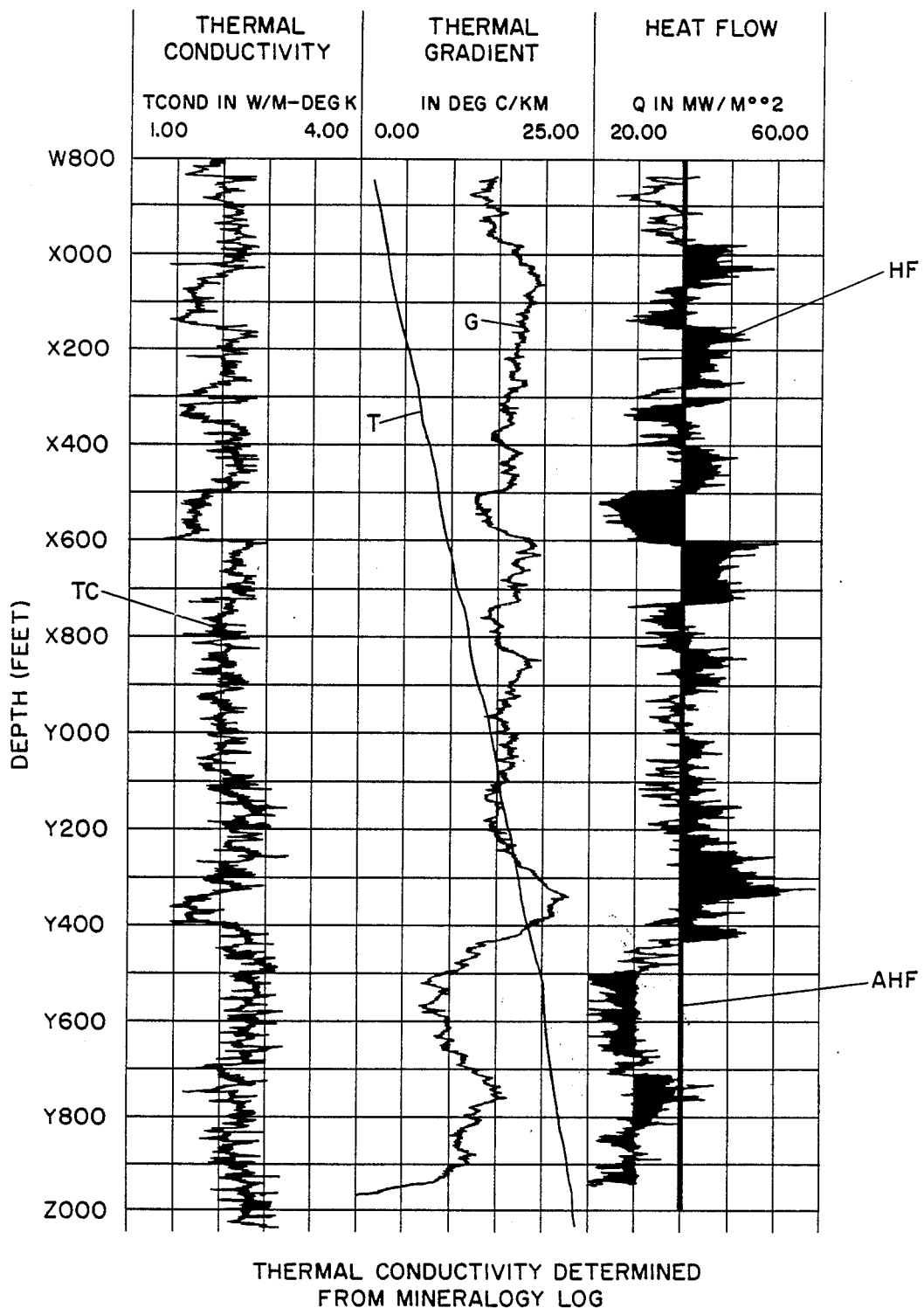
FIG. 3 shows (left) the thermal conductivity determined from the model (see also FIG. 2) (center), the thermal gradients obtained by thermal logging and (right) the heat flow.

Thermal and geochemical logs were run in a thermally stabilized Gulf Coast well off Louisiana. The geochemical logging was performed by a Schlumberger GLT ™ tool and yielded the mineralogy determinations in volume percents shown in FIG. 2. A Schlumberger Auxiliary Measurement Sonde (AMS) was run with the GLT ™ to obtain the thermal log (FIG. 3). The AMS has been run with an ultra-high resolution temperature tool in Ocean Drilling Program wells and has been found to give reliable temperature and thermal gradient measurements. The AMS temperatures are shown as line T in FIG. 3, and the gradients at successive 0.5 foot intervals are shown as line G.

Using the techniques described in Herzog R., L. Colson, B. Seeman, M. O'Brien, H. Scott, D. McKeon, P. Wraight, J. Grau, J. Schweitzer, and M. Herron, "Geochemical Logging with Spectrometry Tools," Society of Petroleum Engineers, Paper 16792, 1987, referred to above, a matrix inversion of the elemental abundances was used to calculate the mineralogy model for the well (FIG. 2). The sand-shale sequences that form the prolific hydrocarbon producers in the area can be easily identified from quartz variations in the mineralogy logs.

As Herzog et al. explain, the combination of natural and induced gamma ray spectroscopy logs measures relative concentrations of Ca, Si, Fe, S, Ti, Gd, Na+Mg, and absolute concentrations of K, U, Th, Al. The application of a closure model (a requirement that the weight percent sum of all elements equal 100%) yields absolute weight percent oxides, for all of the measured elements, with acceptable accuracy for most rocks. The oxide data are used to derive a quantitative mineralogical profile through a matrix inversion scheme which solves for mineral abundances in terms of the mineral elemental formulas. The mineral volume profiles can be accurate to within ±5% by volume as long as the initial matrix model includes the correct set of significant minerals and does not attempt to distinguish between minerals with nearly identical chemical formulas (e.g., amphibole and pyroxene). The calculation of whole-rock thermal conductivity from the resulting continuous mineral volume curves follows the same technique used for mineral counts from thin section analyses (Williams et al., 1988). The mineral volumes are included in a geometric mean model for the thermal conductivity of a crystalline aggregate of known porosity according to the relation $$\lambda \text{ total} = \lambda_1^{\phi_1 *} \lambda_2^{\phi_2 *} \ldots * \lambda_n^{100\, n}$$

where $\lambda_1$ is the thermal conductivity of the first of n constituent minerals and $\phi_1$ is the volume fraction of the first mineral.

Figure 1:
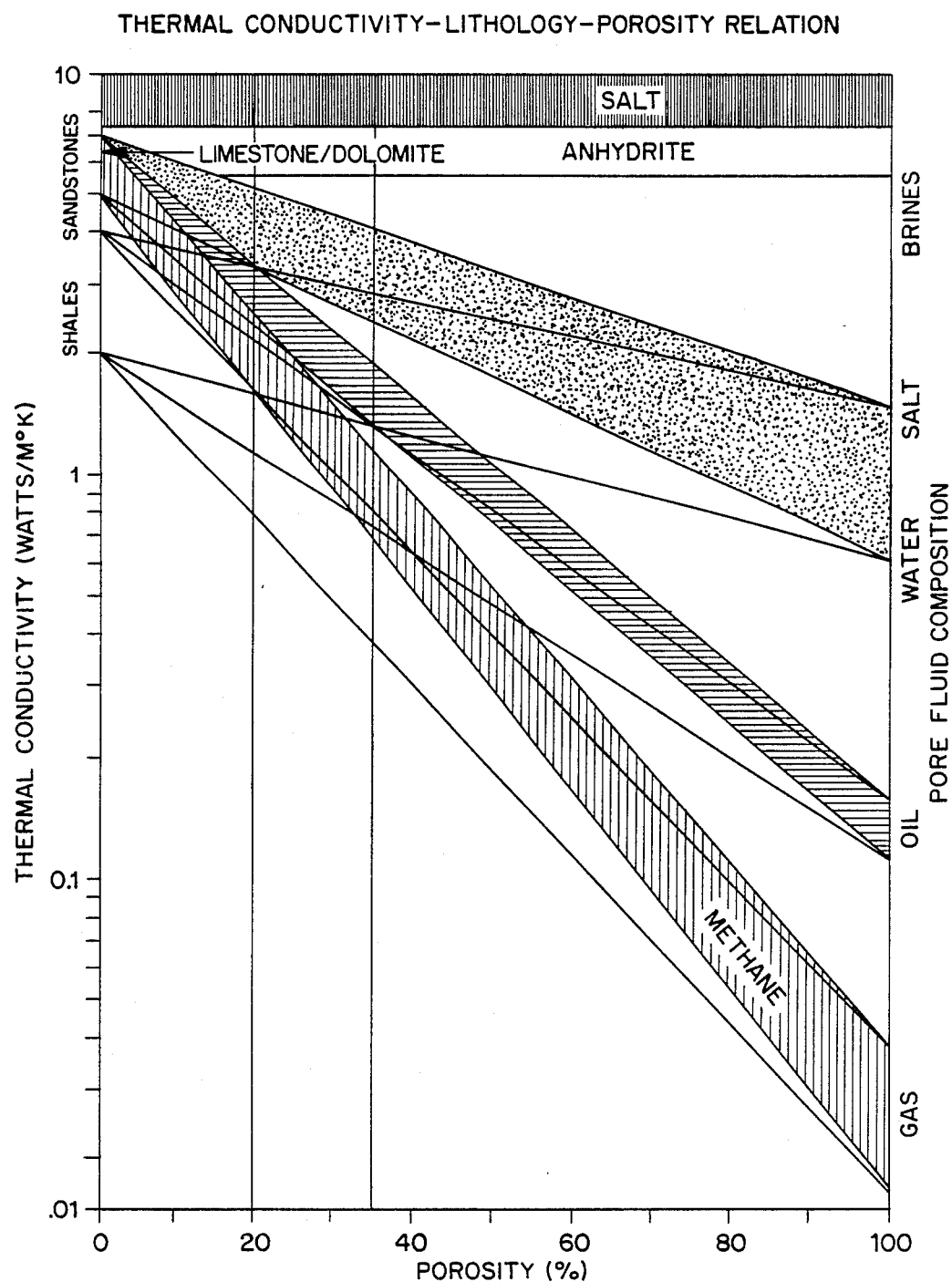
FIG. 1 is a graph showing the general relationship between lithology, pore fluid composition and thermal conductivity and is prepared from laboratory measurements of core samples.

The thermal conductivities of the intervals were calculated from the mineralogy model using the above-described techniques and are plotted in FIGS. 2 and 3. The calculations are based on assumed ideal thermal conductivity values for each principal mineral component of the model. High thermal conductivities are predicted in the sand-rich intervals, and low thermal conductivities are assumed for the shale-rich zones. FIG. 1 provides guidance for the selections, as does the knowledge that Gulf Coast sediments have porosities in the range of from 20% to 35% (range marked in FIG. 1). From FIG. 1, it is to be noted that sandstone lithologies within this range of porosity will have thermal conductivities lower by about 50% for oil-bearing formations and by about 100% for gas-bearing formations, as compared to water-bearing formations. The ideal values of thermal conductivity for the sand-rich intervals are based on the assumption that such intervals are water-bearing. The shaliness is overcompensated for in the calculations by including the water from hydroxyls that are bound within the clays as additional porosity and by using a thermal conductivity appropriate for an unconsolidated clay. The values of ideal thermal conductivity (in W/m°K.) used in this example were as follows: kaolinite—2.8; illite—1.8; smectite—2.0; feldspar—2.2; quartz—7.7, and limestone—3.6.

Line TC (FIGS. 2 and 3) is a plot of the ideal thermal conductivities at the 0.5 foot intervals of the mineral abundances surrounding the wellbore calculated from the mineralogy model and the assumed ideal conductivities of the constituents of the mineralogy model. The heat flow plotted as line HF in FIG. 3 is the simple arithmetic product of the thermal gradient and the ideal thermal conductivity and is an "ideal heat flow" in that it (a) assumes that no oil or gas is present in the formations around the wellbore and (b) compensates for that assumption by assigning low values to shale-rich formations.

Heat productions were calculated from the absolute abundances of the radiogenic elements, potassium, uranium and thorium, measured by a Natural Gamma Spectroscopy Tool and were found to be unimportant in the well of this example. If important they would be added directly to the wellbore heat flow at each depth.

A calculation of the average heat flow for all intervals was found to agree with surface heat flow measurements made in the area by a shipboard surveying team from Lamont-Doherty Geological Observatory (Columbia University). The average heat flow of 36 mW/m$^2$ is shown as solid line AHF in FIG. 3. Below Y500 feet in the well, the average heat flow (26 mW/m$^2$) is clearly lower than the average heat flow above that level. As described below, the change in heat flow below Y500 occurs at the top of geopressure and is caused by fluid convection in the area.

The thermal conductivities of oil-bearing and gas-bearing formations are considerably lower than the thermal conductivities of mineralogically similar formations having saline waters as the pore fluid (FIG. 1). Consequently, the ideal heat flows (FIG. 3) determined at each interval of the well based on assumed high ideal values (water as the pore fluid) of thermal conductivity for the sand-rich mineral components should be artificially high relative to the average heat flow for those intervals where hydrocarbons are present. Also, intervals in gas-prone zones should exhibit ideal heat flows greater than those of oil-bearing formations.

Indeed, several hydrocarbon rich zones are predicted by such high heat flow intervals in the wellbore heat flow log (FIG. 3). It is important to note that these intervals do not always correspond to thermal gradient anomalies (FIG. 3). For example, the hydrocarbon-bearing interval at X600-X720 feet is also a thermal gradient anomaly, but that at X150-X250 feet is not (FIG. 3). Even in the region of the well below Y500 feet with lower average heat flow, relatively high heat flow anomalies indicate hydrocarbons are present from Y700 to Y800 feet.

Figure 4:
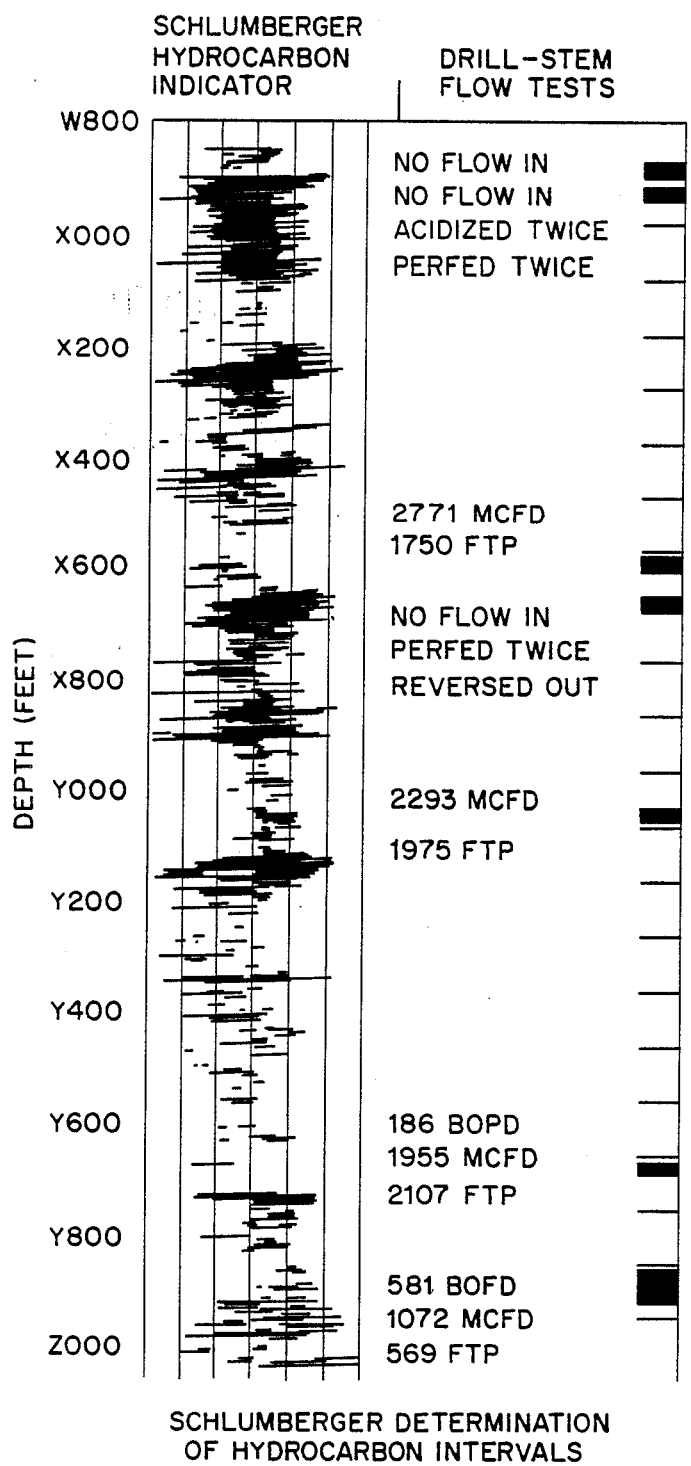
FIG. 4 shows (left) the results of drill-stem flow tests and (right) hydrocarbon indicators from a Schlumberger analysis made completely independently of the present method.

The plot in FIG. 4 on the far right contains the hydrocarbon-bearing zones predicted by the Schlumberger analysis of the well derived from mineralogy and resistivity logs. This analysis is completely independent of the identification of hydrocarbon-bearing intervals by wellbore heat flow analysis. The two analyses generally agree (e.g., at X200, X400, X600, and X850 feet), but the wellbore heat flow determination suggests that the hydrocarbon-bearing zone picked by Schlumberger at W850 to X050 feet extends only from W975 to X050 feet. In drill-stem flow tests in the well (FIG. 4, left), there was no flow at perforations made at W900-W920 and W930-W950 feet, which may have been selected at depths that were too shallow (FIG. 4). Flow-tests at X600-X620 verify predictions from both methods of the presence of abundant hydrocarbons. This interval is characterized by low-above-high heat flow. The low apparent heat flow above X600 is caused, in part, by selection of low thermal conductivity values for wet clays. However, the temperature gradients are low in this shale-rich interval, indicating a possible thermal disturbance from fluid movements, as well. The high apparent heat flow below X600 feet is thought to be indicative of the presence of abundant hydrocarbons, i.e., an anomaly in the ideal heat flow (FIG. 3) resulting from assuming water as the pore fluid in sand-rich intervals.

There is only a small ideal heat flow anomaly to indicate the hydrocarbons found in the flow-tests at Y100 feet. The cause of the small magnitude of the high heat flow anomaly is due to the presence of shales within the sands, which lowers the heat flow. A major producing zone seen in the heat flow at Y250 to Y410 feet was not perforated (see FIG. 4, left). The oil-show at Y710 feet, confirmed by drill-stem flow tests (FIG. 4), is in an interval with a high ideal heat flow anomaly that is much stronger than the hydrocarbon indicator from the Schlumberger analysis at that depth.

The lower average heat flow in the part of the well below Y500 feet is of particular hydrological interest, because thermal convection and fluid migration must be occurring in this interval in order to maintain such a disequilibrium, heat flow contrast across this boundary. Pore fluid salinities, derived from Capture-Sigma measured by the geochemical logging tool and electrical resistivity from the dual induction log, show a significant increase in salinity across this boundary at Y500 feet in the well. Salinities of up to 250,000 ppm are predicted.

The interval below Y500 feet contains both lower heat flow and more saline fluids than the interval above this boundary. FIG. 3 shows that the lower heat flow is not from lower thermal conductivity, but from lower temperature gradients (a change in the slope of the temperature versus depth curve T can be seen to occur at Y500 feet). Thus, the interval contains colder, more dense fluids compared to the hotter, lighter pore fluids found above this boundary; this is a classic geopressure indication in the Gulf Coast.

We claim:

1. A method of locating oil and gas horizons in a wellbore comprising the steps of obtaining by thermal logging temperatures at successive intervals in the wellbore and establishing from said temperatures thermal gradients for said intervals free of drilling-induced thermal disturbances, identifying the mineral abundances surrounding the wellbore at each of said intervals, establishing ideal thermal conductivities for said mineral abundances based on assumptions that sand-rich formations have high thermal conductivities and are water-bearing and that shale-rich formations have low conductivities, determining an ideal heat flow at each interval by multiplying the thermal gradient at such interval by the ideal thermal conductivity of the mineral abundances at the interval, determining the average ideal heat flow for all of the intervals, and identifying the zones of the wellbore exhibiting anomalous ideal heat flows that are higher than the average heat flow.

2. The method according to claim 1 wherein the wellbore is thermally logged at a time sufficiently long after drilling has ceased for thermal disturbances caused by drilling to have dissipated.

3. The method according to claim 1 wherein the wellbore is thermally logged at least twice at an interval of time between such logs sufficient for thermal disturbances caused by drilling to partially dissipate during such time interval and the thermal gradients are established by identifying and correcting for drilling-induced disturbances.

4. The method according to claim 1 wherein the mineral abundances are identified from core or cutting samples taken from the wellbore.

5. The method according to claim 1 wherein the mineral abundances are identified by geochemical logging of the wellbore.

6. The method according to claim 5 wherein the ideal thermal conductivities are obtained by calculations from a mineralogy model created from the logs of the mineral abundances.

* * * * *